US00PP32609P2

(12) United States Plant Patent
Nederpel

(10) Patent No.: US PP32,609 P2
(45) Date of Patent: Dec. 8, 2020

(54) ***ALOE* PLANT NAMED 'NEDALVER'**

(50) Latin Name: *Aloe vera*
Varietal Denomination: NEDALVER

(71) Applicant: Nederpel Succelenten B.V., Honselersdijk (NL)

(72) Inventor: Maurice Nederpel, Honselersdijk (NL)

(73) Assignee: Nederpel Succelenten B.V., Honselersdijk (NL)

( * ) Notice: Subject to any disclaimer, the term of this patent is extended or adjusted under 35 U.S.C. 154(b) by 0 days.

(21) Appl. No.: 16/873,585

(22) Filed: May 14, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct variety of *Aloe* plant named 'NEDALVER' which is characterized by a plurality of succulent foliar rosettes borne on short stems, foliage which is held upright, light green foliage bearing light yellow-green protuberances on the lower leaf surface, large light green spine-like teeth along the leaf margins, and the stability of these characteristics from generation to generation.

4 Drawing Sheets

Latin name of the genus and species: The Latin name of the genus and species of the novel variety disclosed herein is *Aloe vera.*

Variety denomination: The inventive variety of *Aloe* disclosed herein has been given the variety denomination 'NEDALVER'.

BACKGROUND OF THE INVENTION

Parentage: 'NEDALVER' originated as a naturally occurring, whole-plant mutation of an unnamed and unpatented *Aloe vera* plant. In the summer of 2014 the inventor discovered the mutation at a commercial greenhouse in Honselersdijk, the Netherlands, growing amongst a cultivated population of the unnamed *Aloe vera* plant. The mutation was noted for its unique foliage color and growth habit and was subsequently isolated for further evaluation in order to confirm the distinctness and stability of the characteristics first observed. Upon confirmation of distinctness and stability, 'NEDALVER' was selected for commercialization.

Asexual Reproduction: Asexual reproduction of the new cultivar 'NEDALVER', by way of rooting leaf cuttings, was first initiated in the summer of 2014 at the inventor's commercial greenhouse in Honselersdijk, the Netherlands. Through five subsequent generations, the unique features of this cultivar have proven to be stable and true to type.

SUMMARY OF THE INVENTION

The cultivar 'NEDALVER' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'NEDALVER'. These characteristics in combination distinguish 'NEDALVER' as a new and distinct *Aloe vera* plant:

1. 'NEDALVER' exhibits a obovate plant profile with a plurality of foliar rosettes borne on short stems; and
2. 'NEDALVER' exhibits light green succulent foliage which is held upright; and
3. 'NEDALVER' exhibits coarsely dentate leaf margins with an abundance of spine-like teeth that are colored in between yellow-green and green-white, generally appearing as a light green coloration; and
4. 'NEDALVER' exhibits a moderate abundance of light yellow-green round protuberances on the lower leaf surface.

BOTANICAL DESCRIPTION OF THE PLANT

Figure 1:
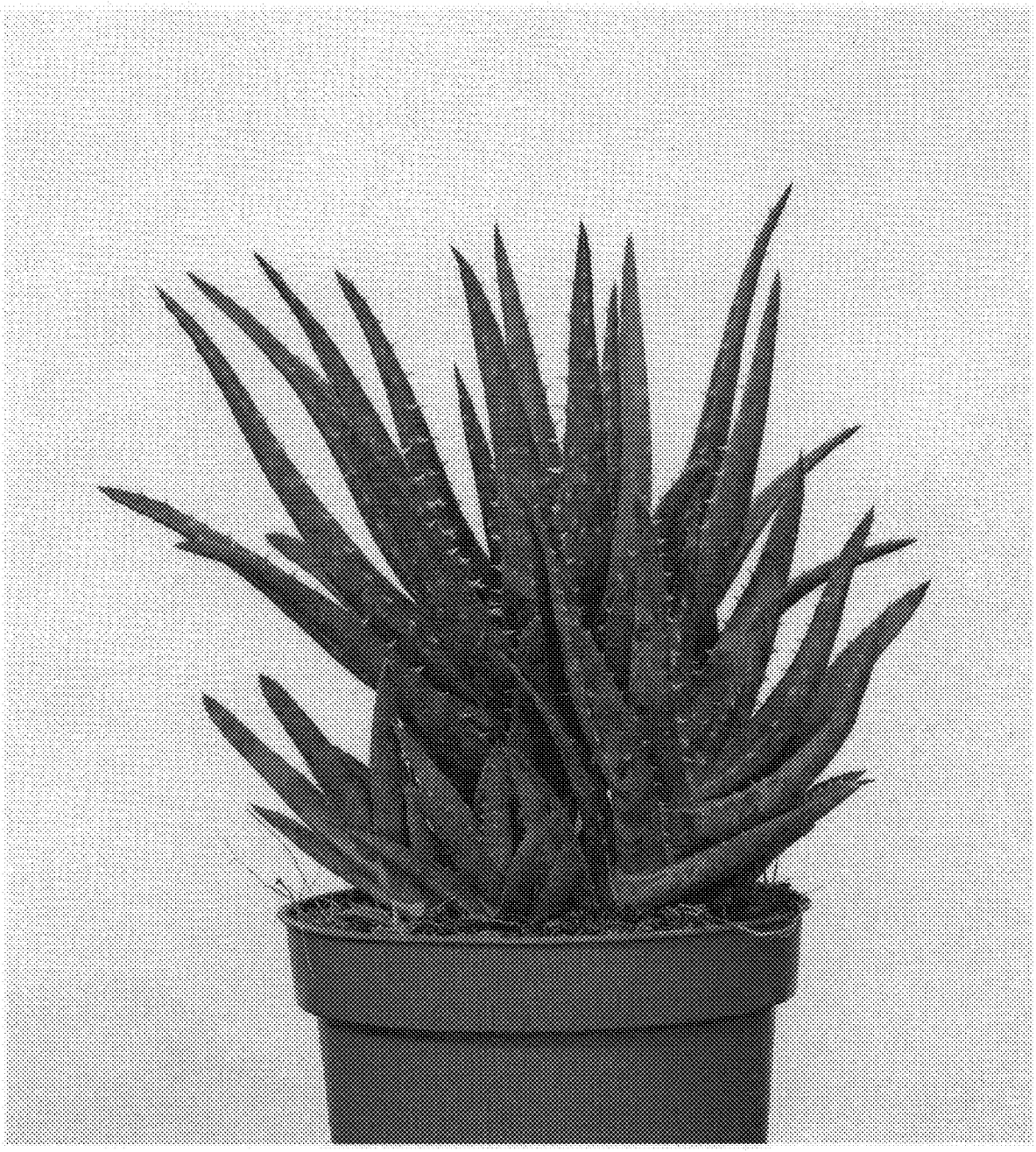
FIG. 1 illustrates, as nearly true as it is reasonably possible to make the same in color photographs of this type, an exemplary plant of 'NEDALVER' grown in a commercial greenhouse in Honselersdijk, the Netherlands. This plant is approximately 12 months old, shown planted in a 10.5 cm container.
Figure 2:
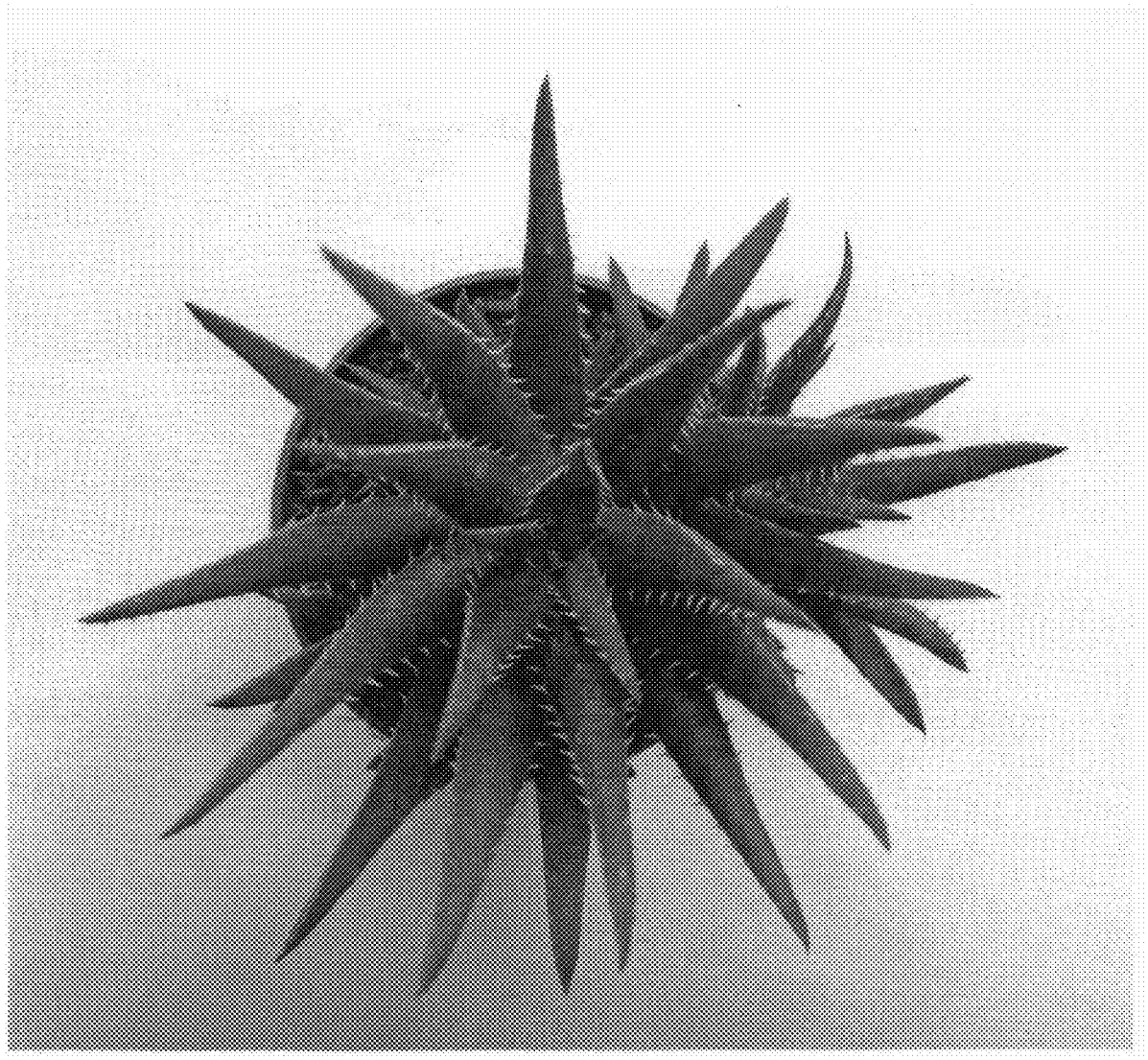
FIG. 2 illustrates, as nearly true as it is reasonably possible to make the same in color photographs of this type, the typical foliage arrangement of 'NEDALVER'.
Figure 3:
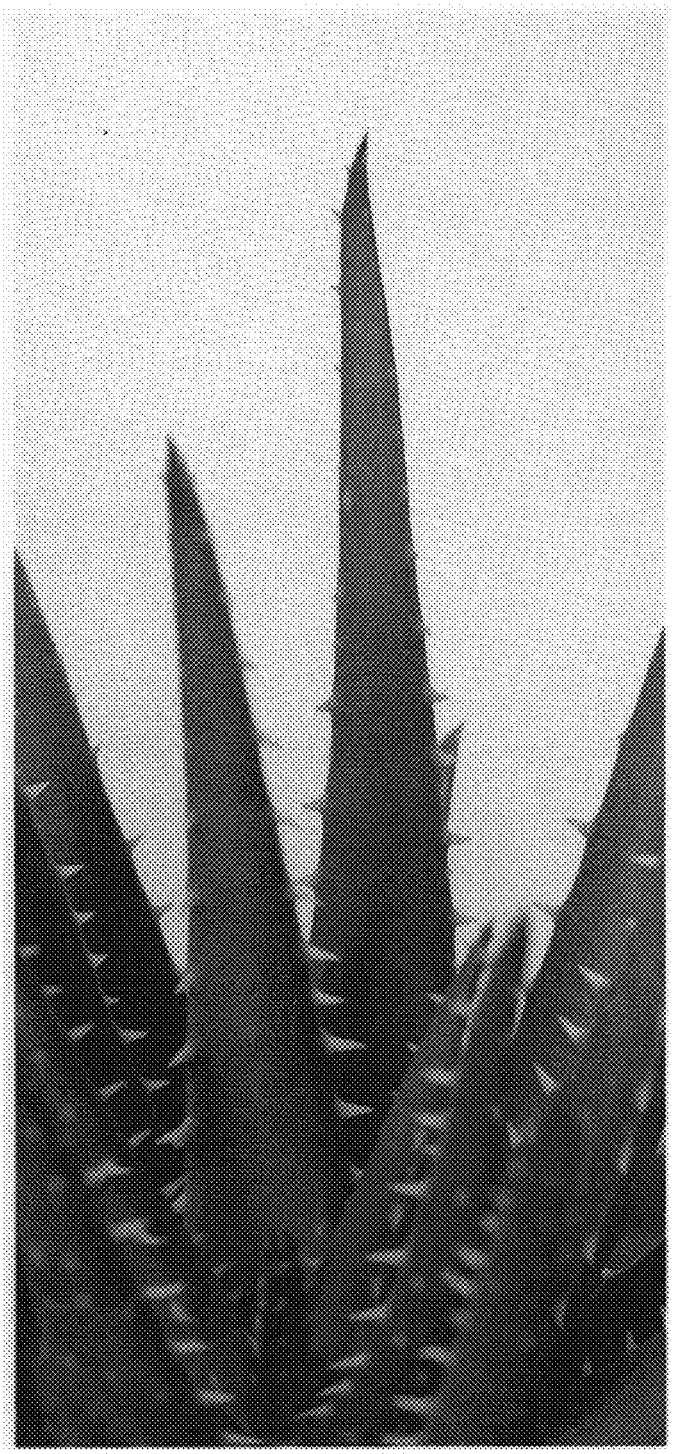
FIG. 3 illustrates, as nearly true as it is reasonably possible to make the same in color photographs of this type, adaxial surface of the mature foliage 'NEDALVER'.
Figure 4:
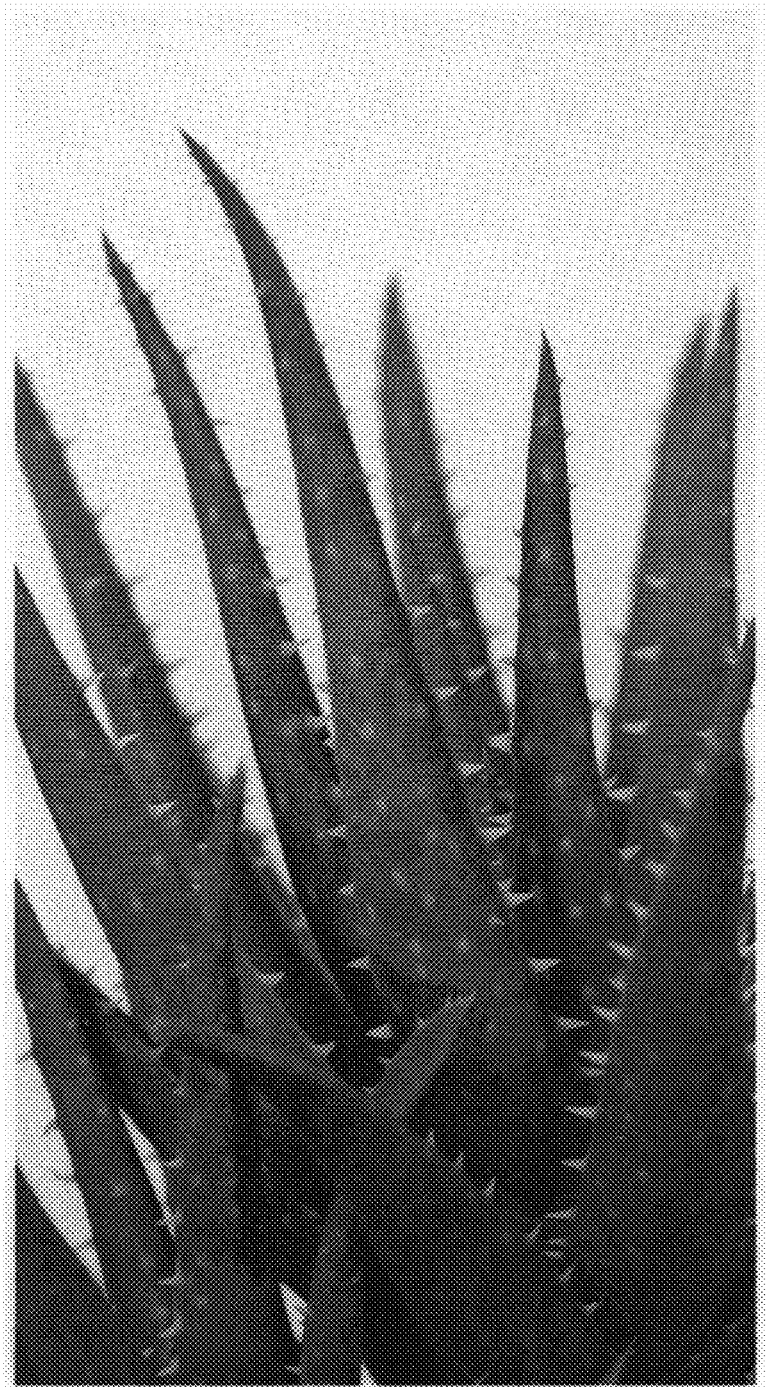
FIG. 4 illustrates, as nearly true as it is reasonably possible to make the same in color photographs of this type, the abaxial surface of the mature foliage of 'NEDALVER'.

The following observations and measurements made in October of 2019 describe averages from a sample set of six specimens of 12 month-old 'NEDALVER' plants grown in 10.5 cm nursery containers at commercial greenhouse in Honselersdijk, the Netherlands. Plants were produced using conventional greenhouse production protocols for *Aloe* which consisted of minimal overhead irrigation, no fertilizer applications, and no chemical pest and disease control measures. No photoperiodic treatments or artificial light was given to the plants.

Those skilled in the art will appreciate that certain characteristics will vary with older or, conversely, with younger plants. 'NEDALVER' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'NEDALVER' and a comparison with the parent and closest known comparator is provided below.

Plant description:

*Growth habit*.—Succulent perennial with foliage growing in a basal rosette, eventually producing a short stem; secondary rosettes are eventually produced at the base, themselves eventually forming a short stem.

*Plant shape*.—Obovate.

*Height from soil level to top of foliar plane*.—14.5 cm.

*Plant spread*.—Average of 16.3 cm.

*Growth rate*.—Moderately fast.

*Plant vigor*.—Moderately to highly vigorous.

*Propagation*.—Type — Leaf cuttings. Time to initiate rooting — Approximately 42 days at 21 degrees Celsius. Crop time — Approximately 9 months to produce a marketable plant in a 9 cm container.

*Disease and pest resistance or susceptibility*.—Neither resistance nor susceptibility to typical *Aloe vera* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—One main stem with lateral branches arising near the base.

*Quantity of main stems*.—1.

*Quantity of lateral branches*.—14.

*Dimensions of the main stem*.—7.0 cm long and 1.2 cm in diameter.

*Internode length of the main stem*.—0.3 cm.

*Aspect*.—Rounded.

*Attitude*.—Main stem is near vertical; lateral branches are at an approximate angle of 45 degrees to the main stem.

*Strength*.—Strong.

*Texture and luster*.—Smooth, glabrous, and slightly glossy.

*Color when developing*.—Yellow-green, nearest to RHS 145D.

*Mature color*.—Yellow-green, nearest to RHS 145C, with darker radial bands, nearest to RHS 146C, and fine axial stripes which are green, nearest to RHS 143B.

*Color at internodes*.—Yellow-green, nearest to RHS 145C, and finely axially striped green, nearest to RHS 143B.

Foliage:

*Arrangement*.—Spiraled.

*Division*.—Simple.

*Attachment*.—Sessile.

*Quantity*.—Approximately 21 leaves per rosette.

*Shape*.—Lanceolate.

*Dimensions*.—10.4 cm long, 2.0 cm wide, and 1.0 cm thick, on average.

*Aspect*.—Flattened terete.

*Attitude*.—Upward and outward at an approximate angle of 50 degrees to nearly 90 degrees from horizontal.

*Apex*.—Narrow acuminate.

*Base*.—Broad cuneate; decurrent. Sheathed portion of the leaf base — Dimensions — 2.4 cm long and 2.1 cm wide. Color — Translucent; yellow-green, nearest to RHS 146D, and fading to green-white towards the margins, nearest to RHS 157D; axially striped with a darker shade of yellow-green at the base, nearest to RHS N144A.

*Margin*.—Coarsely dentate. Teeth have an average length of 0.2 mm; teeth are translucent and colored nearest to in between yellow-green and green-white, RHS 145D and 157A. Margins are not undulated or lobed.

*Texture, adaxial surface*.—Smooth, glabrous and glaucescent.

*Texture, abaxial surface*.—Glabrous, glaucescent, and moderately covered with small, round protuberances that are irregularly arranged on the leaf surface; protuberance are approximately 0.15 cm tall and 0.1 cm in diameter.

*Luster, adaxial surface*.—Matte.

*Luster, abaxial surface*.—Matte.

*Color*.—Juvenile foliage, adaxial surface — Green, nearest to RHS 143A; the epicuticular wax covering the leaf surface is greyed-green, nearest to in between RHS 189A and 189B. Juvenile foliage, abaxial surface — Green, nearest to RHS 143A yet darker; the epicuticular wax covering the leaf surface is greyed-green, nearest to in between RHS 189A and 189B; protuberances are yellow-green, nearest to RHS 144C. Mature foliage, adaxial surface — Green, nearest to RHS 137B; the epicuticular wax covering the leaf surface is greyed-green, nearest to RHS 189B. Mature foliage, abaxial surface — Green, nearest to RHS 137B; the epicuticular wax covering the leaf surface is greyed-green, nearest to RHS 189B; protuberances are yellow-green, nearest to RHS 144C.

*Venation*.—Pattern — Parallel. Color, adaxial surface — Nearest to in between green and yellow-green, RHS NN137B and 147A. Color, abaxial surface — Nearest to in between green and yellow-green, RHS NN137B and 147A.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'NEDALVER' differ from the parent, an unnamed *Aloe vera* plant (not patented), in the following characteristics described in Table 1 below.

TABLE 1

| Characteristic | 'NEDALVER' | The parent |
|---|---|---|
| Foliage width. | Narrower than the parent. | Wider than 'NEDALVER'. |
| General coloration of the mature foliage. | Lighter shade of green. | Darker shade of green. |
| Shape of the foliar protuberances. | Rounded. | Elliptic to linear. |

COMPARISONS WITH THE CLOSEST KNOWN COMPARATOR

Plants of the new cultivar 'NEDALVER' differ from the commercial variety, *Aloe* 'OVROCKS04' (U.S. Plant Pat. No. 30,004) in the following characteristics described in Table 2 below.

TABLE 2

| Characteristic | 'NEDALVER' | 'OVROCKS04' |
|---|---|---|
| Foliage width. | Narrower than 'OVROCKS04'. | Wider than 'NEDALVER'. |
| Foliage margins. | Coarsely dentate with light green spine-like teeth. | Coarsely dentate with white spine-like teeth. |
| General coloration of the mature foliage. | Lighter shade of green. | Darker shade of green. |

That which is claimed is:

1. A new and distinct variety of *Aloe vera* plant named 'NEDALVER', substantially as described and illustrated herein.

* * * * *